United States Patent
Candau

(10) Patent No.: US 7,402,301 B2
(45) Date of Patent: *Jul. 22, 2008

(54) SUNSCREEN COMPOSITIONS COMPRISING METAL OXIDE MINERAL PIGMENTS AND HYDROXYALKYLUREA COMPOUNDS

(75) Inventor: Didier Candau, Bievres (FR)

(73) Assignee: L'Oreal, Paris (FR)

( * ) Notice: Subject to any disclaimer, the term of this patent is extended or adjusted under 35 U.S.C. 154(b) by 232 days.

This patent is subject to a terminal disclaimer.

(21) Appl. No.: 11/311,650

(22) Filed: Dec. 20, 2005

(65) Prior Publication Data

US 2006/0177396 A1    Aug. 10, 2006

Related U.S. Application Data

(60) Provisional application No. 60/646,598, filed on Jan. 26, 2005.

(30) Foreign Application Priority Data

Dec. 20, 2004   (FR) .................................. 04 53078

(51) Int. Cl.
*A61Q 17/04*   (2006.01)
*A61Q 17/00*   (2006.01)
*A61Q 19/04*   (2006.01)
*A61Q 19/00*   (2006.01)
*A61K 8/02*    (2006.01)

(52) U.S. Cl. .......................... 424/59; 424/60; 424/400; 424/401

(58) Field of Classification Search .................. 424/59, 424/60, 400, 401
See application file for complete search history.

(56) References Cited

FOREIGN PATENT DOCUMENTS

| DE | 2703185 A1 | 8/1978 |
|---|---|---|
| EP | 1 535 607 A1 | 6/2005 |
| WO | WO 02/005546 A1 | 7/2002 |

OTHER PUBLICATIONS

Anonymous, "Moisturization Synergy of Hydroxylkylurea in Combination with at least one or more other moisturizing agents", IP Com Journal, 2004, pp. 1-9, IP Com Inc., West Henrietta, NY.
International Search Report corresponding to EP 05 29 2562, issued on Mar. 20, 2006, 4 pages.
French Search Report corresponding to FR 04/53078, issued on Aug. 4, 2005, 1 page.

*Primary Examiner*—Shelley A. Dodson
(74) *Attorney, Agent, or Firm*—Buchanan, Ingersoll & Rooney, PC

(57) ABSTRACT

The invention relates to a composition comprising, in a cosmetically acceptable carrier, a system for screening out UV radiation, characterized in that it contains:
(a) at least metal oxide-based mineral pigments, and
(b) at least one hydroxyalkylurea of formula (I) below:

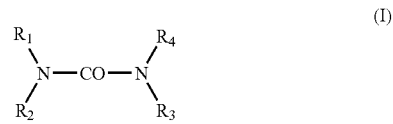

(I)

in which $R_1$, $R_2$, $R_3$ and $R_4$ each independently represent a hydrogen atom, a $C_1$-$C_4$ alkyl group or a $C_2$-$C_6$ hydroxy-alkyl group that may contain from 1 to 5 hydroxyl groups, at least one of the radicals $R_1$-$R_4$ representing a hydroxyalkyl group, and also a salt, solvate or isomer thereof, said composition containing no kojic dipalmitate.

The invention also relates to the use of a hydroxyalkylurea of formula (I) in a composition comprising, in a cosmetically acceptable carrier, at least metal oxide-based mineral pigments, for reducing, or even eliminating, the whitening effect on the keratin material after application.

19 Claims, No Drawings

SUNSCREEN COMPOSITIONS COMPRISING METAL OXIDE MINERAL PIGMENTS AND HYDROXYALKYLUREA COMPOUNDS

CROSS-REFERENCE TO PRIORITY/PROVISIONAL APPLICATIONS

This application claims priority under 35 U.S.C. § 119 of FR 04/53078, filed Dec. 20, 2004, and of provisional application Ser. No. 60/646,598, filed Jan. 26, 2005, each hereby expressly incorporated by reference and each assigned to the assignee hereof.

CROSS-REFERENCE TO COMPANION APPLICATIONS

Copending application Ser. No. 11/311,451, Ser. No. 11/311,450, Ser. No. 11/311,448, and Ser. No. 11/311,691, concurrently herewith, each hereby expressly incorporated by reference and each assigned to the assignee hereof.

BACKGROUND OF THE INVENTION

1. Technical Field of the Invention

The invention present relates to sunscreen compositions comprising, formulated into a cosmetically acceptable carrier, at least one system for screening out UV radiation, and containing:
 (a) at least metal oxide mineral pigment, and
 (b) at least one specific hydroxyalkylurea compound.

2. Description of Background and/or Related and/or Prior Art

It is well known that light radiation with wavelength of from 280 nm to 400 nm permits tanning of the human epidermis and that rays with wavelengths of from 280 to 320 nm, which are known as UV-B rays, cause skin burns and erythema that can harm the development of a natural tan; this UV-B radiation should therefore be screened out.

It is also known that UV-A rays, with wavelengths of from 320 to 400 nm, which cause tanning of the skin, are liable to induce an impairment in the skin, especially in the case of sensitive skin or skin that is continually exposed to solar radiation. UV-A rays in particular bring about a loss of elasticity of the skin and the appearance of wrinkles, leading to premature aging. They promote the triggering of the erythemal reaction or amplify this reaction in certain individuals and may even be the cause of phototoxic or photoallergic reactions. It is therefore desirable also to screen out UV-A radiation.

UV-A and UV-B rays should therefore be screened out, and cosmetic compositions for protecting the human epidermis containing UV-A- and UV-B-screening agents currently exist.

The UV-screening agents most commonly used are organic and soluble in oils or in aqueous media; they generally have, within their structure, a chromophore group linked to a solubilizing group, which is generally a fatty chain in the case of liposoluble UV-screening agents or else a carboxylic or sulfonic acid group in the case of water-soluble UV-screening agents.

Many cosmetic compositions intended for photoprotection of the skin have been proposed to date, and the use of metal oxide nanopigments, such as $TiO_2$ nanopigments, in anti-sun products is increasingly common since they make it possible to obtain very high protection indices in combination with conventional UV-screening agents.

The anti-sun compositions are quite often in the form of an emulsion, of oil-in-water type (i.e., a cosmetically and/or dermatologically acceptable carrier consisting of a continuous aqueous dispersing phase and of a discontinuous fatty dispersed phase), or of water-in-oil type (aqueous phase dispersed in a continuous fatty phase), which contains, in varying concentrations, one or more conventional lipophilic organic screening agents and/or conventional hydrophilic organic screening agents capable of selectively absorbing the harmful UV radiation, these screening agents (and the amounts thereof being selected as a function of the desired sun protection factor, the sun protection factor (SPF) being expressed mathematically as the ratio of the dose of UV radiation required to reach the erythema-forming threshold with the UV-screening agent to the dose of the UV radiation required to reach the erythema-forming threshold without the UV-screening agent. In such emulsions, the hydrophilic screening agents are present in the aqueous phase and the lipophilic screening agents are present in the fatty phase.

One of the major drawbacks of the anti-sun compositions known to date that contain metal oxide, in particular titanium oxide, mineral pigments is that, once applied to the skin in the form of a film, they engender, on the latter, a whitening effect that is cosmetically undesirable and in general not very well liked by users. The higher the concentration of pigments in the composition, the more marked this effect is. In order to prevent this problem, it would, of course, be possible to use reduced amounts of pigments, but the resulting emulsions, which would admittedly result in an acceptable transparency on the skin, would then no longer offer suitable protection in the UV range, which greatly limits the advantage of such an operation.

Another difficulty lies in the fact that conventional anti-sun emulsions based on protective pigments produce, after application to the skin, an uneven, nonhomogeneous, or even coarse, distribution of the pigments on this skin, which may be harmful to the quality of the overall photoprotective effect. This poor pigment distribution that is observed at the surface of the skin is often linked to the fact that, in terms of the initial composition itself (before application), there is a substantial lack of homogeneity (poor dispersion of the pigment in its carrier).

The inclusion of titanium oxide pigments (Tioveil AQ) in a depigmenting lotion containing kojic dipalmitate has already been proposed. This formulation does not make it possible to remedy the technical problems mentioned above.

SUMMARY OF THE INVENTION

After considerable research in the field of photoprotection, it has now unexpectedly and surprisingly been determined that it is possible to remedy or ameliorate the various drawbacks indicated above by combining metal oxide mineral pigments with a hydroxyalkylurea of formula (I) more fully described hereinafter. The anti-sun/sunscreen compositions containing such a combination also exhibit good anti-sun effectiveness, good water remanence, perspiration remanence and washing remanence, and also good persistence over time.

This discovery forms the basis of the present invention.

In the remainder of the present description, the expression "system for screening out UV radiation" means an agent for screening out UV radiation, comprising either a single organic or inorganic compound for screening out UV radiation, or a mixture of several organic or inorganic compounds for screening out UV radiation, for example a mixture comprising a UV-A-screening agent and a UV-B-screening agent.

Thus, the present invention features compositions comprising, formulated into cosmetically acceptable carrier, at least one system for screening out UV radiation, and which comprises:

(a) at least metal oxide mineral pigment, and
(b) at least one hydroxyalkylurea of formula (I) more fully described hereinafter, such compositions containing no kojic palmitate.

The present invention also features the use of a hydroxyalkylurea of formula (I) more fully described hereinafter, in a composition comprising, in a cosmetically acceptable carrier, at least metal oxide-based mineral pigments, for reducing, or even eliminating, the whitening effect on the keratin material (such as the skin, eyelashes, eyebrows, nails or mucous membranes) after application.

Other characteristics, aspects and advantages of the invention will become apparent from the detailed description that will follow.

DETAILED DESCRIPTION OF BEST MODE AND SPECIFIC/PREFERRED EMBODIMENTS OF THE INVENTION

The pigments in accordance with the invention preferably have a mean elemental particle size of greater than 5 nm and less than 100 nm. According to a particularly preferred embodiment of the invention, this size preferably ranges from 10 nm to 50 nm.

The pigments may be coated or uncoated.

The coated pigments are pigments that have undergone one or more surface treatments of chemical, electronic, mechanochemical and/or mechanical nature with compounds as described, for example, in *Cosmetics & Toiletries*, February 1990, Vol. 105, p. 53-64, such as amino acids, beeswax, fatty acids, fatty alcohols, anionic surfactants, lecithins, sodium, potassium, zinc, iron or aluminum salts of fatty acids, metal alkoxides (titanium or aluminum alkoxides), polyethylene, silicones, proteins (collagen, elastin), alkanolamines, silicon oxides, metal oxides or sodium hexametaphosphate.

In a known manner, the silicones are organosilicon polymers or oligomers having a linear or cyclic, branched or crosslinked structure, of variable molecular weight, obtained by polymerization and/or polycondensation of silanes that are suitably functionalized, and consisting mostly of a repetition of main units in which the silicon atoms are connected to one another by oxygen atoms (siloxane bond), optionally substituted hydrocarbon-based radicals being directly linked via a carbon atom to said silicon atoms.

The term "silicones" also encompasses the silanes required for their preparation, in particular alkyl silanes.

The silicones used for coating the nanopigments that are suitable for the present invention are preferably selected from the group consisting of alkyl silanes, polydialkylsiloxanes and polyalkylhydrogenosiloxanes. Even more preferably, the silicones are selected from the group consisting of octyl trimethyl silane, polydimethylsiloxanes and polymethylhydrogenosiloxanes.

Of course, the metal oxide pigments, before their treatment with silicones, may have been treated with other surface agents, in particular with cerium oxide, alumina, silica, aluminum compounds, silicon compounds, or mixtures thereof.

The coated pigments are more particularly titanium oxides coated:

with silica, such as the product "Sunveil" from Ikeda,
with silica and with iron oxide, such as the product "Sunveil F" from Ikeda,
with silica and with alumina, such as the products "Microtitanium Dioxide MT 500 SA" and "Microtitanium Dioxide MT 100 SA" from Tayca, and "Tioveil" from Tioxide,
with alumina, such as the products "Tipaque TTO-55 (B)" and "Tipaque TTO-55 (A)" from Ishihara, and "UVT 14/4" from Kemira,
with alumina and with aluminum stearate, such as the product "Microtitanium Dioxide MT 100 T, MT 100 TX, or MT 100 Z" from Tayca,
with alumina and with aluminum laurate, such as the product "Microtitanium Dioxide MT 100 S" from Tayca,
with iron oxide and with iron stearate, such as the product "Microtitanium dioxide MT 100 F" from Tayca,
with zinc oxide and with zinc stearate, such as the product "BR351" from Tayca,
with silica and with alumina, and treated with a silicone, such as the products "Microtitanium Dioxide MT 600 SAS", "Microtitanium Dioxide MT 500 SAS" or "Microtitanium Dioxide MT 100 SAS" from Tayca,
with silica, with alumina and with aluminum stearate, and treated with a silicone, such as the product "STT-30-DS" from Titan Kogyo,
with alumina and treated with a silicone, such as the products "Tipaque TTO-55 (S)" from Ishihara, or "UV Titan M 262" from Kemira,
with triethanolamine, such as the product "STT-65-S" from Titan Kogyo,
with stearic acid, such as the product "Tipaque TTO-55 (C)" from Ishihara,
with sodium hexametaphosphate, such as the product "Microtitanium Dioxide MT 150 W" from Tayca.

Other titanium oxide pigments treated with a silicone are preferably $TiO_2$ treated with octyl trimethyl silane, the mean elemental particle size of which is from 25 to 40 nm, such as that marketed under the trademark "T 805" by Degussa Silices, $TiO_2$ treated with a polydimethylsiloxane, the mean elemental particle size of which is 21 nm, such as that marketed under the trademark "70250 Cardre UF TiO2SI3" by Cardre, or anatase/rutile $TiO_2$ treated with a polydimethylhydrogenosiloxane, the mean elemental particle size of which is 25 nm, such as that marketed under the trademark "Microtitanium Dioxide USP Grade Hydrophobic" by Color Techniques.

The uncoated titanium oxide pigments are, for example, marketed by Tayca under the trademarks "Microtitanium Dioxide MT 500 B" or "Microtitanium Dioxide MT 600 B", by Degussa under the name "P 25", by Wackher under the name "Oxyde de titane transparent PW", by Miyoshi Kasei under the name "UFTR", by Tomen under the name "ITS" and by Tioxide under the name "Tioveil AQ".

The uncoated zinc oxide pigments are, for example:
those marketed under the name "Z-Cote" by Sunsmart;
those marketed under the name "Nanox" by Elementis;
those marketed under the name "Nanogard WCD 2025" by Nanophase Technologies.

The coated zinc oxide pigments are, for example:
those marketed under the name "Oxide Zinc CS-5" by Toshibi (ZnO coated with polymethylhydrogenosiloxane);
those marketed under the name "Nanogard Zinc Oxide FN" by Nanophase Technologies (as a 40% dispersion in Finsolv TN, $C_{12}$-$C_{15}$ alkyl benzoate);
those marketed under the name "Daitopersion ZN-30" and "DAITOPERSION ZN-50" by Daito (dispersions in cyclopolymethylsiloxane/oxyethylenated polydimethylsiloxane, containing 30% or 50% of zinc nanooxides coated with silica and polymethylhydrogenosiloxane);

those marketed under the name "NFD Ultrafine ZNO" by Daikin (ZnO coated with perfluoroalkyl phosphate and a perfluoroalkylethyl-based copolymer as a dispersion in cyclopentasiloxane);

those marketed under the name "SPD-Z1" by Shin-Etsu (ZnO coated with a silicone-grafted acrylic polymer dispersed in cyclodimethylsiloxane);

those marketed under the name "Escalol Z100" by ISP (ZnO treated with alumina and dispersed in the mixture ethylhexyl methoxycinnamate/PVP-hexadecene copolymer/methicone);

those marketed under the name "Fuji ZNO-SMS-10" by Fuji Pigment (ZnO coated with silica and polymethylsilsesquioxane);

those marketed under the name "Nanox Gel TN" by Elementis (ZnO dispersed at 55% in $C_{12}$-$C_{15}$ alkyl benzoate with hydroxystearic acid polycondensate).

The uncoated cerium oxide pigments are marketed under the name "Colloidal Cerium Oxide" by Rhone Poulenc.

The uncoated iron oxide nanopigments are, for example, marketed by Arnaud under the names "Nanogard WCD 2002 (FE 45B)", "Nanogard Iron FE 45 BL AQ", "Nanogard FE 45R AQ", "Nanogard WCD 2006 (FE 45R)", or by Mitsubishi under the name "TY-220".

The coated iron oxide pigments are, for example, marketed by Arnaud under the names "Nanogard WCD 2008 (FE 45B FN)", "Nanogard WCD 2009 (FE 45B 556)", "Nanogard FE 45 BL 345" or "Nanogard FE 45 BL", or by BASF under the name "Oxyde De Fer Transparent".

Mention may also be made of the mixtures of metal oxides, in particular of titanium dioxide and of cerium dioxide, including the equal-weight mixture of silica-coated titanium dioxide and cerium dioxide, marketed by Ikeda under the name "Sunveil A", and also the mixture of titanium dioxide and of zinc dioxide coated with alumina, silica and silicone such as the product "M 261" marketed by Kemira or coated with alumina, silica and glycerol such as the product "M 211" marketed by Kemira.

According to the invention, the coated or uncoated titanium oxide pigments are particularly preferred.

The titanium oxide may be in rutile, anatase or amorphous form, but preferably in rutile and/or anatase and/or amorphous or substantially amorphous form.

The pigments in accordance with the invention generally represent from 0.5 to 40%, preferably from 1 to 30%, of the total weight of the emulsion.

The hydroxyalkylureas in accordance with the invention are selected from among those corresponding to general formula (I):

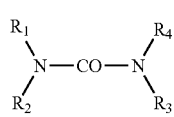

in which $R_1$, $R_2$, $R_3$ and $R_4$ each independently represent a hydrogen atom, a $C_1$-$C_4$ alkyl radical or a $C_2$-$C_6$ hydroxyalkyl radical containing from 1 to 5 hydroxyl groups, at least one of the radicals $R_1$-$R_4$ representing a hydroxyalkyl group, and also the salts, solvates and isomers thereof.

In formula (I), among the alkyl radicals, mention may in particular be made of methyl, ethyl, n-propyl, isopropyl, n-butyl, isobutyl and tert-butyl radicals.

The compounds of formula (I) that are preferred are those that contain only one hydroxyalkyl group, i.e., those for which $R_1$ is a hydroxyalkyl group and $R_2$, $R_3$ and $R_4$ represent, independently of one another, a hydrogen atom or a $C_1$-$C_4$ alkyl group. The compounds of formula (I) for which $R_1$ is a hydroxyalkyl radical and $R_2$, $R_3$ and $R_4$ each represent a hydrogen atom are more particularly preferred.

Among the hydroxyalkyl groups, preference is given to those containing a single hydroxyl group, and in particular hydroxyethyl, hydroxypropyl, hydroxybutyl, hydroxypentyl and hydroxyhexyl groups. The hydroxyethyl group is preferred.

As compounds of formula (I) that are preferred, mention may be made of N-(2-hydroxyethyl)urea; N-(2-hydroxypropyl)urea; N-(3-hydroxypropyl)urea; N-(2,3-dihydroxypropyl)urea; N-(2,3,4,5,6-pentahydroxyhexyl)urea; N-methyl-N-(1,3,4,5,6-pentahydroxy-2-hexyl)urea; N-methyl-N'-(1-hydroxy-2-methyl-2-propyl)urea; N-(1-hydroxy-2-methyl-2-propyl)urea; N-(1,3-dihydroxy-2-propyl)urea; N-(trishydroxymethylmethyl)urea; N-ethyl-N'-(2-hydroxyethyl)urea; N,N-bis-(2-hydroxyethyl)urea; N,N'-bis-(2-hydroxyethyl)urea; N,N-bis-(2-hydroxypropyl)urea; N,N'-bis-(2-hydroxypropyl)$_u$ rea; N,N-bis-(2-hydroxyethyl)-N'-propyl urea; N,N-bis-(2-hydroxypropyl)-N'-(2-hydroxyethyl)urea; N-tert-butyl-N'-(2-hydroxyethyl)-N'-(2-hydroxypropyl)urea; N-(1,3-dihydroxy-2-propyl)-N'-(2-hydroxyethyl)urea; N,N-bis-(2-hydroxyethyl)-N',N'-dimethylurea; N,N,N',N'-tetrakis-(2-hydroxyethyl)urea; and N',N'-bis-(2-hydroxyethyl)-N',N'-bis-(2-hydroxypropyl) urea.

A compound that is particularly preferred for use in the present invention is N-(2-hydroxyethyl)urea, hereinafter referred to as "hydroxyethylurea".

The hydroxyalkylureas of formula (I) can be prepared as described in DE-2703185. Among these, hydroxyethylurea is also commercially available, in the form of a mixture at 50% by weight in water, from National Starch under the trademark Hydrovance®.

Among the salts, mention may be made of salts of inorganic acids, such as sulfuric acid, hydrochloric acid, hydrobromic acid, hydriodic acid, phosphoric acid or boric acid. Mention may also be made of the salts of organic acids, which may contain one or more carboxylic, sulfonic or phosphonic acid groups. They may be linear, branched or cyclic aliphatic acids or else aromatic acids. These acids may also contain one or more hetero atoms selected from O and N, for example in the form of hydroxyl groups. Mention may in particular be made of propionic acid, acetic acid, terephthalic acid, citric acid and tartaric acid.

The term "solvate" means a stoichiometric mixture of said compound of formula (I) with one or more molecules of water or of organic solvent, such a mixture being derived from the synthesis of the compound of formula (I).

The hydroxyalkylureas in accordance with the invention are preferably present in the compositions in accordance with the invention at contents of from 0.01 to 50% by weight, and more preferably from 0.1 to 20%, and even more preferably from 0.1 to 10% by weight relative to the total weight of the composition.

The compositions in accordance with the invention will preferably comprise other supplementary organic photoprotective agents, that are active in the UV-A and/or UV-B range and that are hydrophilic or lipophilic or even soluble in the cosmetic solvents commonly used.

The supplementary organic hydrophilic or lipophilic photoprotective agents are in particular selected from anthranilates; dibenzoylmethane derivatives; cinnamic derivatives;

salicylic derivatives; camphor derivatives; benzophenone derivatives; β,β-diphenylacrylate derivatives; triazine derivatives; benzotriazole derivatives; benzylmalonate derivatives, in particular those mentioned in U.S. Pat. No. 5,624,663; benzimidazole derivatives; imidazolines; bis-benzoazolyl derivatives as described in EP-669,323 and U.S. Pat. No. 2,463,264; p-aminobenzoic acid (PABA) derivatives; methylenebis(hydroxyphenyl benzotriazole) derivatives as described in U.S. Pat. Nos. 5,237,071, 5,166,355, GB-2303549, DE-19726184 and EP-893,119; benzoxazole derivatives as described in EP-O-832,642, EP-1-027,883, EP-1-300,137 and DE-10162844; screening polymers and screening silicones such as those described in particular in WO 93/04665; dimers derived from α-alkylstyrene, such as those described in DE-19855649; 4,4-diarylbutadienes as described in EP-O-967,200, DE-19746654, DE-19755649, EP-A-1-008,586, EP-1-133,980 and EP-133,981, and mixtures thereof.

As examples of supplementary organic photoprotective agents, mention may be made of those denoted below under their INCI name:

Para-Aminobenzoic Acid Derivatives:

PABA,

Ethyl PABA,

Ethyl dihydroxypropyl PABA,

Ethylhexyl dimethyl PABA marketed in particular under the name "Escalol 507" by ISP, Glyceryl PABA, PEG-25 PABA marketed under the name "Uvinul P25" by BASF.

Dibenzoylmethane Derivatives:

Butyl methoxydibenzoylmethane marketed in particular under the trademark "Parsol 1789" by Hoffmann Laroche, Isopropyldibenzoylmethane.

Salicylic Derivatives:

Homosalate marketed under the name "Eusolex HMS" by Rona/EM Industries,

Ethylhexyl salicylate marketed under the name "Neo Heliopan OS" by Haarmann and Reimer, Dipropylene glycol salicylate marketed under the name "Dipsal" by Scher, TEA salicylate marketed under the name "Neo Heliopan TS" by Haarmann and Reimer.

Cinnamic Derivatives:

Ethylhexyl methoxycinnamate marketed in particular under the trademark "Parsol MCX" by Hoffmann La Roche, Isopropyl methoxycinnamate, Isoamyl methoxycinnamate marketed under the trademark "Neo Heliopan E 1000" by Haarmann and Reimer, Cinoxate, DEA methoxycinnamate, Diisopropyl methylcinnamate, Glyceryl ethylhexanoate dimethoxycinnamate.

β,β-Diphenylacrylate derivatives:

Octocrylene marketed in particular under the trademark "Uvinul N539" by BASF,

Etocrylene marketed in particular under the trademark "Uvinul N35" by BASF.

Benzophenone Derivatives:

Benzophenone-1 marketed under the trademark "Uvinul 400" by BASF,

Benzophenone-2 marketed under the trademark "Uvinul D50" by BASF,

Benzophenone-3 or oxybenzone, marketed under the trademark "Uvinul M40" by BASF, Benzophenone-4 marketed under the trademark "Uvinul MS40" by BASF, Benzophenone-5, Benzophenone-6 marketed under the trademark "Helisorb 11" by Norquay, Benzophenone-8 marketed under the trademark "SpectraSorb UV-24" by American Cyanamid, Benzophenone-9 marketed under the trademark "Uvinul DS-49" by BASF, Benzophenone-12, n-Hexyl 2-(4-diethylamino-2-hydroxybenzoyl)benzoate.

Benzylidenecamphor Derivatives:

3-Benzylidenecamphor manufactured under the name "Mexoryl SD" by Chimex,

4-Methylbenzylidenecamphor marketed under the name "Eusolex 6300" by Merck,

Benzylidenecamphorsulfonic acid manufactured under the name "Mexoryl SL" by Chimex, Camphor benzalkonium methosulfate manufactured under the name "Mexoryl SO" by Chimex, Terephthalylidenedicamphorsulfonic acid manufactured under the name "Mexoryl SX" by Chimex, Polyacrylamidomethylbenzylidenecamphor manufactured under the name "Mexoryl SW" by Chimex.

Phenylbenzimidazole Derivatives:

Phenylbenzimidazolesulfonic acid marketed in particular under the trademark "Eusolex 232" by Merck, Disodium phenyl dibenzimidazole tetrasulfonate marketed under the trademark "Neo Heliopan AP" by Haarmann and Reimer.

Phenylbenzotriazole Derivatives:

Drometrizole trisiloxane marketed under the name "Silatrizole" by Rhodia Chimie, Methylenebisbenzotriazolyltetramethylbutylphenol marketed in solid form under the trademark "Mixxim BB/100" by Fairmount Chemical or in micronized form in aqueous dispersion under the trademark "Tinosorb M" by Ciba Specialty Chemicals.

Triazine Derivatives:

Bis-ethylhexyloxyphenol methoxyphenyl triazine marketed under the trademark "Tinosorb S" by Ciba Geigy, Ethylhexyltriazone marketed in particular under the trademark "Uvinul T150" by BASF, Diethylhexylbutamidotriazone marketed under the trademark "Uvasorb HEB" by Sigma 3V, 2,4,6-tris(dineopentyl 4'-aminobenzalmalonate)-s-triazine, 2,4,6-tris(diisobutyl 4'-aminobenzalmalonate)-s-triazine.

Anthranilic Derivatives:

Menthyl anthranilate marketed under the trademark "Neo Heliopan MA" by Haarmann and Reimer,
Imidazoline Derivatives:

Ethylhexyldimethoxybenzylidenedioxoimidazoline propionate.
Benzalmalonate Derivatives:

Dineopentyl 4'-methoxybenzalmalonate,

Polyorganosiloxane containing benzalmalonate functions, such as Polysilicone-15 marketed under the trademark "Parsol SLX" by Hoffmann La Roche.
4,4-Diarylbutadiene Derivatives:
1,1-Dicarboxy(2,2'-dimethylpropyl)-4,4'-diphenylbutadiene.
Benzoxazole Derivatives:

2,4-bis[5-1 (dimethylpropyl)benzoxazol-2-yl(4-phenyl)imino]-6-(2-ethylhexyl)imino-1,3,5-triazine marketed under the name Uvasorb $K_2A$ by Sigma 3V, and mixtures thereof.

The preferred supplementary organic photoprotective agents are selected from among:
Ethylhexyl methoxycinnamate,
Homosalate,
Ethylhexyl salicylate,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Terephthalylidenedicamphorsulfonic acid,
Disodium phenyl dibenzimidazole tetrasulfonate,
Ethylhexyltriazone,
Bis-ethylhexyloxyphenol methoxyphenyl triazine,
Diethylhexylbutamidotriazone,
2,4,6-tris(dineopentyl 4'-aminobenzalmalonate)-s-triazine,
2,4,6-tris(diisobutyl 4'-aminobenzalmalonate)-s-triazine,
Drometrizole trisiloxane,
Polysilicone-15,
Dineopentyl 4'-methoxybenzalmalonate,
1,1-dicarboxy(2,2'-dimethylpropyl)-4,4-diphenylbutadiene,
2,4-bis[5-1 (dimethylpropyl)benzoxazol-2-yl(4-phenyl)imino]-6-(2-ethylhexyl)imino-1,3,5-triazine,
and mixtures thereof.

Among the insoluble organic UV-screening agents, mention may be made of those described in U.S. Pat. Nos. 5,237,071, 5,166,355, GB-2303549, DE-19726184 and EP-893,119, and in particular methylenebis(hydroxyphenyl benzotriazole) derivatives such as the methylenebisbenzotriazolyltetramethylbutylphenol marketed in solid form under the trademark "Mixxim BB/100" by Fairmount Chemical or in micronized form in aqueous dispersion under the trademark "Tinosorb M" by Ciba Specialty Chemicals.

The supplementary inorganic photoprotective agents are selected from pigments (average size of the primary particles: generally from 5 nm to 100 nm, preferably from 10 nm to 50 nm) of metal oxides that are coated or uncoated, such as, for example, pigments of titanium oxide (amorphous or crystallized in rutile and/or anatase form), of iron oxide, of zinc oxide, of zirconium oxide or of cerium oxide, or mixtures thereof. Conventional coating agents are, moreover, alumina and/or aluminum stearate. Such coated or uncoated metal oxide pigments are in particular described in EP-518,772 and EP-518,773.

The additional photoprotective agents are generally present in the compositions according to the invention in proportions ranging from 0.01 to 20% by weight relative to the total weight of the composition, and preferably ranging from 0.1 to 10% by weight relative to the total weight of the composition.

The compositions according to the invention may be in any of the forms suitable for topical application, in particular in the form of aqueous gels, or in the form of emulsions obtained by dispersion of a fatty phase (also called oily phase) in an aqueous phase (O/W), or vice versa (W/O), or of multiple emulsions (for example, W/O/W or O/W/O or O/O/W). They can be more or less fluid and can have the appearance of a white or colored cream, of an ointment, of a milk, of a lotion, of a serum, of a paste, of a powder or of a solid stick, and can optionally be packaged in an aerosol and be in the form of a foam or of a spray. These compositions are prepared according to the usual methods.

According to a particular embodiment of the invention, the composition according to the invention is in the form of an emulsion and then comprises at least one oily phase. The proportion of the oily phase of the emulsion can range from 1 to 80% by weight, preferably from 2 to 50% by weight, and better still from 2 to 40% by weight, relative to the total weight of the composition. The fatty substances of the oily phase, in particular the oils, and the emulsifiers and coemulsifiers optionally present, used in the composition in the form of an emulsion, are selected from those conventionally used in cosmetics or dermatology. The emulsifier and the coemulsifier, when they are present, are generally so in a proportion ranging from 0.1 to 30% by weight, preferably from 0.3 to 20% by weight, and better still from 0.5 to 15% by weight, relative to the total weight of the composition. The emulsion may also contain lipid vesicles in addition to or instead of the emulsifiers and/or coemulsifiers.

Depending on their more or less pronounced lipophilic, or conversely hydrophilic, nature, the nanopigments may be present either in the fatty phase of the emulsion, or in the aqueous phase, or even in the two phases at once.

The emulsions generally contain at least one emulsifier selected from amphoteric, anionic, cationic or nonionic emulsifiers, used alone or as a mixture. The emulsifiers are selected in an appropriate manner according to the continuous phase of the emulsion to be obtained (W/O or O/W). When the emulsion is a multiple emulsion, it generally comprises an emulsifier in the primary emulsion and an emulsifier in the external phase into which the primary emulsion is introduced.

As emulsifiers that can be used for preparing the W/O emulsions, mention may, for example, be made of alkyl esters or ethers of sorbitan, of glycerol or of sugars; silicone surfactants, for instance dimethicone copolyols, such as the mixture of cyclomethicone and of dimethicone copolyol, marketed under the names DC 5225 C and DC 3225 C by Dow Corning, and alkyldimethicone copolyols such as the laurylmethicone copolyol marketed under the name "Dow Corning 5200 Formulation Aid" by Dow Corning, cetyidimethicone copolyol marketed under the name Abil EM 90® by Goldschmidt and the mixture of polyglyceryl-4 isostearate/cetyldimethicone copolyol/hexyl laurate, marketed under the name Abil WE 09® by Goldschmidt. One or more coemulsifiers may also be added thereto, which coemulsifiers may advantageously be selected from the group comprising branched-chain fatty acid esters of polyol, and especially branched-chain fatty acid esters of glycerol and/or of sorbitan, for example polyglyceryl isostearate, such as the product marketed under the name Isolan GI 34 by Goldschmidt, sorbitan isostearate, such as the product marketed under the name Arlacel 987 by ICI, and sorbitan glyceryl isostearate, such as the product marketed under the name Arlacel 986 by ICI, and mixtures thereof.

As emulsifiers that can be used for preparing the O/w emulsions, mention may, for example, be made of nonionic emulsifiers such as oxyalkylenated (more particularly polyoxyethylenated) fatty acid esters of polyols, for example polyethylene glycol stearates, for instance PEG-100 stearate, PEG-50 stearate and PEG-40 stearate; oxyalkylenated fatty acid esters of sorbitan comprising, for example, from 20 to 100 EO, and for example those marketed under the trademarks Tween 20 or Tween 60 by Uniqema; oxyalkylenated (oxyethylenated and/or oxypropylenated) fatty alcohol ethers; alkoxylated or non-alkoxylated sugar esters, for instance sucrose stearate and PEG-20 methylglucose sesquistearate; sorbitan esters such as the sorbitan palmitate marketed under the name Span 40 by Uniqema; esters of diacid and of fatty alcohol, such as dimyristyl tartrate; mixtures of these emulsifiers, for instance the mixture of glyceryl stearate and of PEG-100 stearate (CTFA name: glycerylstearate/PEG-100 stearate) marketed under the name Arlacel 165 by Uniqema and under the name Simulsol 165 by Seppic; or the mixture of dimyristyl tartrate, of cetearyl alcohol, of Pareth-7 and of PEG-25 laureth-25, marketed under the name Cosmacol PSE by Sasol (CTFA name: dimyristyl tartrate/cetearyl alcohol/12-15 Pareth 7/PPG 25 laureth 25).

Coemulsifiers may be added to these emulsifiers, for instance fatty alcohols containing from 8 to 26 carbon atoms, for instance cetyl alcohol, stearyl alcohol and the mixture thereof (cetearyl alcohol), octyldodecanol, 2-butyloctanol, 2-hexyldecanol, 2-undecylpentadecanol or oleyl alcohol, or fatty acids.

Emulsions free of emulsifying surfactants or containing less than 0.5% thereof relative to the total weight of the composition may also be prepared, by using suitable compounds for stabilizing said emulsions, for example amphiphilic polymers, fillers, thickeners or gelling agents.

When the composition of the invention is in emulsion form, it comprises at least one oily phase that contains at least one oil, in particular a cosmetic oil. The term "oil" means a fatty substance that is liquid at room temperature (25° C.).

As oils that can be used in the compositions of the invention, use may, for example, be made of hydrocarbon-based oils of animal origin, such as perhydrosqualene (or squalane); hydrocarbon-based oils of plant origin, such as caprylic/capric acid triglycerides, for instance those marketed by Stearineries Dubois or those marketed under the names Miglyol 810, 812 and 818 by Dynamit Nobel, or alternatively oils of plant origin, for example sunflower oil, corn oil, soybean oil, marrow oil, grapeseed oil, sesame oil, hazelnut oil, apricot oil, macadamia oil, arara oil, coriander oil, castor oil, avocado oil, jojoba oil or shea butter oil; synthetic oils; silicone oils, for instance volatile or non-volatile polymethylsiloxanes (PDMS) containing a linear or cyclic silicone chain, which are liquid or pasty at ambient temperature; fluoro oils, such as partially hydrocarbon-based and/or partially silicone-based fluoro oils, for instance those described in document JP-A-2-295912; ethers such as dicaprylyl ether (CTFA name: dicaprylyl ether); and $C_{12}$-$C_{15}$ fatty alcohol benzoates (Finsolv TN from Finetex); arylalkyl benzoate derivatives such as 2-phenylethyl benzoate (from ISP); amidated oils such as isopropyl N-lauroylsarcosinate (Eldew SL-205 from Ajimoto), and mixtures thereof.

The oily phase may also comprise one or more fatty substances selected, for example, from fatty alcohols (cetyl alcohol, stearyl alcohol, cetearyl alcohol), fatty acids (stearic acid) or waxes (paraffin, polyethylene wax, carnauba wax, beeswax).

The compositions of the invention may also contain one or more organic solvents which may be selected from the group consisting of hydrophilic organic solvents, lipophilic organic solvents, amphiphilic solvents, or mixtures thereof.

Among the hydrophilic organic solvents, mention may, for example, be made of linear or branched monohydric alcohols containing from 1 to 8 carbon atoms, such as ethanol, propanol, butanol, isopropanol or isobutanol; polyethylene glycols containing from 6 to 80 ethylene oxides; polyols such as propylene glycol, isoprene glycol, butylene glycol, glycerol or sorbitol; monoalkyl or dialkyl isosorbide in which the alkyl groups contain from 1 to 5 carbon atoms, such as dimethyl isosorbide; glycol ethers, such as diethylene glycol monomethyl ether or diethylene glycol monoethyl ether, and propylene glycol ethers such as dipropylene glycol methyl ether.

As amphiphilic organic solvents, mention may be made of polypropylene glycol (PPG) derivatives, such as esters of polypropylene glycol and of a fatty acid, or of PPG and of a fatty alcohol, for instance PPG-23 oleyl ether and PPG-36 oleate.

As lipophilic organic solvents, mention may, for example, be made of fatty esters such as diisopropyl adipate, dioctyl adipate or alkyl benzoates.

The compositions in accordance with the present invention may also comprise conventional cosmetic adjuvants selected from softeners, humectants, opacifiers, stabilizers, emollients, silicones, anti-foams, fragrances, preserving agents, anionic, cationic, nonionic, zwitterionic or amphoteric surfactants, fillers, polymers, propellants, basifying or acidifying agents, or any other ingredient normally used in cosmetics and/or dermatology.

As hydrophilic thickeners, mention may be made of carboxyvinyl polymers such as carbopols (carbomers) and Pemulen (acrylate/$C_{10}$-$C_{30}$ alkyl acrylate copolymer); cellulose derivatives such as hydroxyethyl-cellulose; polysaccharides, and in particular gums such as xanthan gum; and mixtures thereof.

As lipophilic thickeners, mention may be made of modified clays such as hectorite and derivatives thereof, for instance the products marketed under the name Bentone.

As preserving agents, mention may be made of para-hydroxybenzoic acid esters, also called Parabens® (in particular methyl paraben, ethyl paraben, propyl paraben), phenoxyethanol, compounds which release formaldehyde, such as, for example, imidazolidinylurea or diazolidinylurea, chlorhexidine digluconate, sodium benzoate, caprylyl glycol, iodopropynyl butyl carbamate, pentylene glycol, alkyltrimethylammonium bromide, such as myristyltrimethylammonium bromide (CTFA name: myrtrimonium bromide), dodecyltrimethylammonium bromide, hexadecyltrimethylammonium bromide, and mixtures thereof, such as the mixture marketed under the name Cetrimide® by FEF Chemicals. The preserving agent may be present in the composition according to the invention at a content ranging from 0.001 to 10% by weight, relative to the total weight of the composition, especially ranging from 0.1 to 5% by weight, and in particular ranging from 0.2 to 3% by weight.

As fillers that may be incorporated in the compositions of the invention, mention may, for example, be made of pigments; silica powder; talc; polyamide particles, and in particular those marketed under the name Orgasol by Atochem; polyethylene powders; powders of natural organic materials such as starch powders, in particular powders of crosslinked or non-crosslinked cornstarch, wheat starch or rice starch, such as the starch powders crosslinked with octenylsuccinate anhydride marketed under the name Dry-Flo by National Starch; microspheres based on acrylic copolymers, such as those made of ethylene glycol dimethacrylate/lauryl methacrylate copolymer marketed by Dow Corning under the name Polytrap; polymethyl methacrylate powders such as those marketed under the name Micropearl M 100 by Matsumoto; expanded powders such as hollow microspheres, and in particular the microspheres marketed under the name Expancel by Kemanord Plast or under the name Micropearl F 80 ED by Matsumoto; silicone resin microbeads such as those marketed under the name Tospearl by Toshiba Silicone; polyurethane powders such as the hexamethylene diisocyanate/trimethylol hexyl lactone copolymer powder marketed under the name Plastic Powder D-400 by Toshiba Pigment (CTFA name: HDI/trimethylol hexyllactone crosspolymer); and mixtures thereof. When they are present, these fillers may be in amounts ranging from 0.001 to 20% by weight, preferably from 0.1 to 10% by weight, and better still from 1 to 5% by weight, relative to the total weight of the composition.

Of course, one skilled in this art will take care to choose the possible supplementary compound(s) mentioned above and/or the amounts thereof in such a way that the advantageous properties intrinsically associated with the combination in accordance with the invention are not, or are not substantially, impaired by the envisaged addition(s).

The compositions according to the invention are generally suitable for topical application to the skin and therefore generally comprise a physiologically acceptable medium, i.e., a medium compatible with the skin and/or its integuments. It is preferably a cosmetically acceptable medium, i.e., a medium that has a pleasant color, odor and feel and that does not generate any unacceptable discomfort (stinging, tautness, redness) that may dissuade the consumer from using this composition.

The compositions according to the invention may constitute a skincare product, in particular for the face, the neck, the area around the eyes or the body; alternatively a skin makeup product such as a complexion product (especially a foundation), an eyeshadow, a blusher, an eyeliner, a concealer product, a body makeup product, an anti-sun product or else a skin cleansing product. Preferably, the composition according to the invention will be an anti-sun product.

The composition is generally not rinsed off, but it may be rinsed off if it constitutes a cleansing product, in particular a foaming product.

The present invention also features a cosmetic regime or regimen for treating a keratin material such as the skin, the eyelashes, the eyebrows, the nails or the mucous membranes, characterized in that a composition as defined above is applied to the keratin material.

According to another aspect, this invention also features a cosmetic assembly comprising:

i) a container delimiting at least one compartment, said container being closed by means of a closing member; and ii) a composition as described above and placed inside said compartment.

The container may be in any appropriate form. It may in particular be in the form of a bottle, a tube, a jar, a case, a box, a sachet or a carton.

The closing member may be in the form of a removable stopper, a lid, a cap, a tear-off strip or a capsule, in particular of the type comprising a body attached to the container and a cover cap articulated on the body. It may also be in the form of a member for selectively closing the container, in particular a pump, a valve or a flap valve.

The product may be contained directly in the container, or indirectly. By way of example, the product may be arranged on an impregnated carrier, in particular in the form of a wipe or of a pad, and arranged (individually or in plurality) in a box or in a sachet. Such a carrier incorporating the product is described, for example, in WO 01/03538.

The closing member may be coupled to the container by screwing. Alternatively, the coupling between the closing member and the container is done other than by screwing, in particular via a bayonet mechanism, by click-fastening, gripping, welding, bonding or by magnetic attraction. The term "click-fastening" is in particular intended to mean any system involving the crossing of a bead or cord of material by elastic deformation of a portion, in particular of the closing member, followed by return to the elastically unconstrained position of said portion after the crossing of the bead or cord.

The container may be at least partially made of thermoplastic material. By way of examples of thermoplastic materials, mention may be made of polypropylene or polyethylene.

Alternatively, the container is made of non-thermoplastic material, in particular of glass or of metal (or alloy).

The container may have rigid walls or deformable walls, in particular in the form of a tube or of a tubular bottle.

The container may comprise means for distributing or facilitating the distribution of the composition. By way of example, the container may have deformable walls so as to cause the composition to exit in response to a positive pressure inside the container, this positive pressure being caused by elastic (or non-elastic) squeezing of the walls of the container.

The compositions according to the invention may be in the form of sprayable fluid lotions in accordance with the invention that are applied to the skin or the hair in the form of fine particles by means of pressurization devices. The devices in accordance with the invention are well known to those skilled in the art and comprise non-aerosol pumps or "atomizers", aerosol containers comprising a propellant and also aerosol pumps that use compressed air as propellant. The latter are described in U.S. Pat. Nos. 4,077,441 and 4,850,517.

The compositions packaged as an aerosol in accordance with the invention generally contain conventional propellants such as, for example, hydrofluoro compounds, dichlorodifluoromethane, difluoroethane, dimethyl ether, isobutane, n-butane, propane or trichlorofluoromethane. They are preferably present in amounts ranging from 15 to 50% by weight relative to the total weight of the composition.

In order to further illustrate the present invention and the advantages thereof, the following specific examples are given, it being understood that same are intended only as illustrative and in nowise limitative. In said examples to follow, all parts and percentages are given by weight, unless otherwise indicated.

The following anti-sun formulations were prepared; the amounts are indicated as percentages by weight:

| Compositions | Ex 1 | Ex 2 | Ex 3 | Ex 4 | Ex 5 |
|---|---|---|---|---|---|
| PHASE A: | | | | | |
| Polydimethylsiloxane | 0.5 | 0.5 | 0.5 | 0.5 | 0.5 |
| Preservatives | 1.0 | 1.0 | 1.0 | 1.0 | 1.0 |
| Stearic acid | 1.5 | 1.5 | 1.5 | 1.5 | 1.5 |
| Mixture of glyceryl monostearate/PEG (100 EO) stearate | 1.0 | 1.0 | 1.0 | 1.0 | 1.0 |
| Mixture of cetylstearyl glucoside/cetylstearyl alcohol | 2.0 | 2.0 | 2.0 | 2.0 | 2.0 |
| $C_{12}/C_{15}$ alcoholbenzoate | 5.0 | — | 5.0 | 5.0 | — |
| Isohexadecane | 1.0 | 1.0 | 1.0 | 1.0 | 1.0 |
| Cetyl alcohol | 0.5 | 0.5 | 0.5 | 0.5 | 0.5 |

-continued

| Compositions | Ex 1 | Ex 2 | Ex 3 | Ex 4 | Ex 5 |
|---|---|---|---|---|---|
| Butyl methoxydibenzoyl-methane | 2.0 | 2.5 | 2.0 | 2.0 | 2.0 |
| Octocrylene | 9.0 | 10.0 | 9.0 | 10.0 | 10.0 |
| Drometrizole trisiloxane | 1.0 | — | 4.0 | — | — |
| Bis-ethylhexyloxyphenol methoxyphenyltriazine | 1.0 | 3.0 | 1.0 | 3.0 | 3.0 |
| Ethylhexyl methoxycinnamate | — | 3.0 | — | 5.0 | 5.0 |
| TiO$_2$ | 3.0 | 5.0 | 3.0 | 5.0 | 5.0 |
| PHASE B: | | | | | |
| N-(2-hydroxyethyl)urea | 5.0 | 10.0 | 5.0 | 5.0 | 10.0 |
| Deionized water | qs 100 | qs 100 | qs 100 | qs 100 | qs 100 |
| Sequestering agent | 0.1 | 0.1 | 0.1 | 0.1 | 0.1 |
| Glycerol | 5.0 | 5.0 | 5.0 | 5.0 | 5.0 |
| Xanthan gum | 0.2 | 0.2 | 0.2 | 0.2 | 0.2 |
| Monocetyl phosphate | 1.0 | 1.0 | 1.0 | 1.0 | 1.0 |
| PHASE C: | | | | | |
| Acrylic acid/stearyl methacrylate copolymer | 0.2 | 0.2 | 0.2 | 0.2 | 0.2 |
| Triethanolamine | qs | qs | qs | qs | qs |

The aqueous phase (phase B) containing all of its ingredients are heated to 80° C. in a water bath. The fatty phase (phase A) containing all of its ingredients are heated to 80° C. in a water bath. A is emulsified in B with stirring of rotor-stator type (device from Moritz). Phase C is incorporated and the mixture is allowed to return to ambient temperature with moderate stirring. The triethanolamine is introduced so as to adjust the pH to the desired value at the end of manufacture.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic composition comprising at least one system for screening out UV radiation, and further comprising:
   (a) at least one metal oxide mineral pigment, and
   (b) at least one hydroxyalkylurea compound of formula (I):

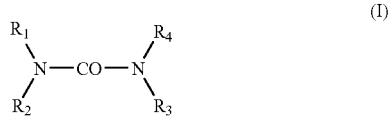

in which $R_1$, $R_2$, $R_3$ and $R_4$ each independently represent a hydrogen atom, a $C_1$-$C_4$ alkyl radical or a $C_2$-$C_6$ hydroxyalkyl radical containing from 1 to 5 hydroxyl groups, at least one of the radicals $R_1$-$R_4$ representing a hydroxyalkyl group, or salt, solvate, or isomer thereof, formulated into (c) a topically applicable, cosmetically acceptable carrier therefor.

2. The cosmetic composition as defined by claim 1, devoid of kojic dipalmitate.

3. The cosmetic composition as defined by claim 1, wherein, in formula (I), $R_1$ is a hydroxyalkyl group and $R_2$, $R_3$ and $R_4$ represent, independently of one another, a hydrogen atom or a $C_1$-$C_4$ alkyl radical.

4. The cosmetic composition as defined by claim 3, wherein, in formula (I), $R_1$ is a hydroxyalkyl group and $R_2$, $R_3$ and $R_4$ each represent a hydrogen atom.

5. The cosmetic composition as defined by claim 1, said at least one compound of formula (I) being selected from the group consisting of N-(2-hydroxyethyl)urea; N-(2-hydroxypropyl)urea; N-(3-hydroxypropyl)urea; N-(2,3-dihydroxypropyl)urea; N-(2,3,4,5,6-pentahydroxyhexyl)urea; N-methyl-N-(1,3,4,5,6-pentahydroxy-2-hexyl)urea; N-methyl-N'-(1-hydroxy-2-methyl-2-propyl)urea; N-(1-hydroxy-2-methyl-2-propyl)urea; N-(1,3-dihydroxy-2-propyl)urea; N-(trishydroxymethylmethyl)urea; N-ethyl-N'-(2-hydroxyethyl)urea; N,N-bis-(2-hydroxyethyl)urea; N,N'-bis-(2-hydroxyethyl)urea; N,N-bis-(2-hydroxypropyl)urea; N,N'-bis-(2-hydroxypropyl)urea; N,N-bis-(2-hydroxyethyl)-N'-propylurea; N,N-bis-(2-hydroxypropyl)-N'-(2-hydroxyethyl)urea; N-tert-butyl-N'-(2-hydroxyethyl)-N'-(2-hydroxypropyl)urea; N-(1,3-dihydroxy-2-propyl)-N'-(2-hydroxyethyl)urea; N,N-bis-(2-hydroxyethyl)-N',N'-dimethylurea; N,N,N',N'-tetrakis-(2-hydroxyethyl)urea; and N',N'-bis-(2-hydroxyethyl)-N',N'-bis-(2-hydroxypropyl) urea; and mixtures thereof.

6. The cosmetic composition as defined by claim 1, wherein said at least one compound of formula (I) is N-(2-hydroxyethyl)urea.

7. The cosmetic composition as defined by claim 1, comprising 0.01 to 50% by weight of said at least one compound of formula (I).

8. The cosmetic composition as defined by claim 1, said at least one metal oxide mineral pigment being selected from the group consisting of coated or uncoated titanium oxide, zinc oxide, iron oxide, cerium oxide, and mixtures thereof.

9. The cosmetic composition as defined by claim 8, comprising nanopigments based on coated or uncoated titanium oxide.

10. The cosmetic composition as defined by claim 9, comprising titanium oxide in rutile, anatase or amorphous form.

11. The cosmetic composition as defined by claim 1, said at least one metal oxide mineral pigment having a mean elemental particle size of greater than 5 nm and less than 100 nm.

12. The cosmetic composition as defined by claim 11, said mean elemental particle size ranging from 10 nm to 50 nm.

13. The cosmetic composition as defined by claim 1, said at least one metal oxide mineral pigment being present in an amount of from 0.5 to 40% by weight thereof.

14. The cosmetic composition as defined by claim 1, formulated as a skincare product, a skin makeup product, an anti-sun/sunscreen product or a skin cleansing product.

15. The cosmetic composition as defined by claim 1, formulated as an anti-sun/sunscreen product.

16. A regime or regimen for photoprotecting a keratin material against the damaging effects of UV radiation, comprising topically applying thereon a cosmetic composition comprising at least one system for screening out UV radiation, and further comprising:
   (a) at least one metal oxide mineral pigment, and
   (b) at least one hydroxyalkylurea compound of formula (I):

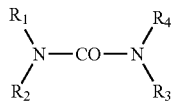 (I)

in which $R_1$, $R_2$, $R_3$ and $R_4$ each independently represent a hydrogen atom, a $C_1$-$C_4$ alkyl radical or a $C_2$-$C_6$ hydroxyalkyl radical containing from 1 to 5 hydroxyl groups, at least one of the radicals $R_1$-$R_4$ representing a hydroxyalkyl group, or salt, solvate or isomer thereof, formulated into (c) a topically applicable, cosmetically acceptable carrier therefor.

17. The regime or regimen as defined by claim 16, said keratin material comprising human skin, hair, eyelashes, eyebrows, nails and/or mucous membranes.

18. The regime or regimen as defined in claim 16, for reducing or eliminating a whitening effect on said keratin material, after application thereon.

19. A cosmetic assembly comprising:
(i) a container delimiting at least one compartment, said container being closed by means of a closing member; and
(ii) a composition as defined by claim 1 and placed inside said compartment.

* * * * *